United States Patent
Hirooka et al.

(10) Patent No.: US 10,283,351 B2
(45) Date of Patent: May 7, 2019

(54) SINGLE-CRYSTAL SILICON CARBIDE SUBSTRATE, METHOD FOR PRODUCING SINGLE-CRYSTAL SILICON CARBIDE SUBSTRATE, AND METHOD FOR INSPECTING SINGLE-CRYSTAL SILICON CARBIDE SUBSTRATE

(71) Applicant: HITACHI METALS, LTD., Minato-ku, Tokyo (JP)

(72) Inventors: Taisuke Hirooka, Tokyo (JP); Hiroyuki Okuda, Tokyo (JP)

(73) Assignee: HITACHI METALS, LTD., Tokyo (JP)

( * ) Notice: Subject to any disclaimer, the term of this patent is extended or adjusted under 35 U.S.C. 154(b) by 0 days.

(21) Appl. No.: 15/006,423

(22) Filed: Jan. 26, 2016

(65) Prior Publication Data
US 2016/0218003 A1    Jul. 28, 2016

(30) Foreign Application Priority Data

Jan. 27, 2015    (JP) .................................. 2015-013216

(51) Int. Cl.
*H01L 21/02*    (2006.01)
*G01N 23/2251*    (2018.01)
(Continued)

(52) U.S. Cl.
CPC ........ *H01L 21/02236* (2013.01); *C30B 29/36* (2013.01); *G01N 23/2251* (2013.01);
(Continued)

(58) Field of Classification Search
CPC ......... H01L 21/02236; H01L 21/02008; H01L 21/02013; H01L 21/02019;
(Continued)

(56) References Cited

U.S. PATENT DOCUMENTS

| 2010/0092366 A1 | 4/2010 | Kogoi et al. | |
|---|---|---|---|
| 2011/0156058 A1* | 6/2011 | Hori | B24B 37/042 257/77 |
| 2013/0032822 A1* | 2/2013 | Ishibashi | H01L 21/02002 257/77 |

FOREIGN PATENT DOCUMENTS

| JP | 2005-064392 | 3/2005 |
|---|---|---|
| JP | 3761546 | 3/2006 |
| JP | 2008-166329 | 7/2008 |
| JP | 2008-227283 | 9/2008 |

(Continued)

OTHER PUBLICATIONS

Yamamoto et al., "Assessment of Stacking Faults in Silicon Carbide Crystals", Sensors and Materials, vol. 25, No. 3 (2013) pp. 177-187.*

(Continued)

*Primary Examiner* — Jonathan C Langman
(74) *Attorney, Agent, or Firm* — Nixon Peabody LLP; Jeffrey L. Costellia (57) ABSTRACT

A single-crystal silicon carbide substrate has a main surface having a surface roughness fulfilling Ra≤1 nm, and has a ratio of hidden scratches of less than 50%, where, in the case where the main surface is arbitrary observed at 50 or more observation points with a field of view having a diameter of 100 μm, the ratio of hidden scratches is defined by a value obtained by dividing the number of the observation points at which a striped hidden scratch having a length of at least 50 μm by the total number of the observation points.

8 Claims, 7 Drawing Sheets

(51) Int. Cl.
*H01L 21/66* (2006.01)
*C30B 29/36* (2006.01)
*H01L 29/16* (2006.01)

(52) U.S. Cl.
CPC .. *H01L 21/02008* (2013.01); *H01L 21/02013* (2013.01); *H01L 21/02019* (2013.01); *H01L 21/02024* (2013.01); *H01L 22/12* (2013.01); *H01L 22/20* (2013.01); *G01N 2223/418* (2013.01); *G01N 2223/634* (2013.01); *H01L 29/1608* (2013.01)

(58) Field of Classification Search
CPC ... H01L 21/02024; H01L 22/12; H01L 22/20; H01L 29/1608; C30B 29/36; G01N 23/2251; G01N 2223/418; G01N 2223/634
See application file for complete search history.

(56) References Cited

FOREIGN PATENT DOCUMENTS

| | | |
|---|---|---|
| JP | 2008-288240 | 11/2008 |
| JP | 2009-294022 | 12/2009 |
| JP | 2010-254576 | 11/2010 |
| JP | 2011-009661 | 1/2011 |
| JP | 2011-220744 | 11/2011 |

OTHER PUBLICATIONS

"Mirror Electron Microscope Technology Having Possibilities of High Speed and Highly Sensitive Inspection", Hitachi Review, Feb. 2012, pp. 46-51.

Hasegawa et al., "Non-destructive observation of in-grown stacking faults in 4H—SiC epitaxial layer using mirror electron microscope", Journal of Applied Physics No. 110, 2011, American Institute of Physics, pp. 073507-1-073508-1.

* cited by examiner

SINGLE-CRYSTAL SILICON CARBIDE SUBSTRATE, METHOD FOR PRODUCING SINGLE-CRYSTAL SILICON CARBIDE SUBSTRATE, AND METHOD FOR INSPECTING SINGLE-CRYSTAL SILICON CARBIDE SUBSTRATE

BACKGROUND OF THE INVENTION

1. Field of the Invention

The present disclosure relates to a single-crystal silicon carbide substrate, a method for producing a single-crystal silicon carbide substrate, and a method for inspecting a single-crystal silicon carbide substrate.

2. Description of the Related Art

A silicon carbide semiconductor has a dielectric breakdown electric field strength, an electron saturated drift velocity, and a thermal conductivity higher than those of a silicon semiconductor. Therefore, research and development has been made to realize power devices using a silicon carbide semiconductor that are capable of performing a large current operation at a higher temperature and a higher speed than those of a conventional silicon device. A motor used for electric bicycles, electric automobiles and hybrid vehicles are AC-driven or inverter-controlled. Development of a highly efficient switching device usable for such uses, among the above-described power devices, is now a target of attention. In order to realize such a power device, a single-crystal silicon carbide substrate on which a high quality silicon carbide semiconductor layer is to be epitaxially grown is necessary.

As disclosed in, for example, Japanese Patent No. 3761546, a single-crystal silicon carbide substrate is produced as follows, like other single crystalline semiconductor substrates. A substrate having a predetermined thickness is cut out from an ingot. After a surface of the substrate is flattened by mechanical polishing, the substrate is processed by chemical mechanical polishing (hereinafter, referred to simply as "CMP") to increase the flatness and the smoothness of the surface thereof to an atomic order. Thus, the single-crystal silicon carbide substrate is produced. However, single crystalline silicon carbide is harder and is more highly corrosion-resistant than other semiconductors. Therefore, single crystalline silicon carbide is not highly processable to be formed into such a substrata, and it is generally difficult to produce a highly smooth single-crystal silicon carbide substrate.

On a single-crystal silicon carbide substrate, a silicon carbide semiconductor layer is formed by epitaxial growth. Therefore, the quality of the silicon carbide semiconductor layer significantly relies on the quality of the surface of the single-crystal silicon carbide substrate. For example, the single-crystal silicon carbide substrate contains stacking faults, dislocation defects or the like. The surface of the single-crystal silicon carbide substrate has, for example, various scratches such as parts denatured by processing, scratches, microscratches or the like. This causes faults or defects in the silicon carbide semiconductor layer.

In order to obtain a single-crystal silicon carbide substrate on which a high quality silicon carbide semiconductor layer is to be epitaxially grown, the surface of such a single-crystal silicon carbide substrate needs to be evaluated so that the above-described defects suppressed.

An example of method for the evaluation is disclosed in Japanese Laid-Open Patent Publication No, 2011-220744. The method is as follows. The surface of the substrate is irradiated with an ultraviolet ray having a predetermined wavelength. From photoluminescence light obtained from the substrate, light of a predetermined wavelength is removed. As a result, a photoluminescence image on the longer wavelength side is obtained. From a brightness difference between this image and a part adjacent thereto, a stacking fault is distinguished.

A scratch or the like at the surface of the single-crystal silicon carbide substrate that forms a part of a processing-derived defect may be observed by an optical method of using, for example, an optical microscope, an optical interference-system surface roughness meter or the like.

SUMMARY OF THE INVENTION

The present inventors have found that conventional single-crystal silicon carbide substrate, even if having a smooth surface, does not have a level of faults or defects (hereinafter, collectively referred to as "defects") in the silicon carbide semiconductor layer that is sufficiently decreased.

The present invention has an object of providing a single-crystal silicon carbide substrate having defects in a silicon carbide semiconductor layer at a further decreased level, a method for producing the same, and a method for inspecting the same.

A single-crystal silicon carbide substrate has a main surface having a surface roughness of $Ra \leq 1$ nm, and has a ratio of hidden scratches of less than 50%, wherein in the case where the main surface is arbitrary observed at 50 or more observation points with field of view having a diameter of 100 μm, the ratio of hidden scratches is defined by a value obtained by dividing the number of the observation points at which a striped bidden scratch having a length of at least 50 μm by the total number of the observation points.

The ratio of hidden scratches may be determined by capturing an image of the main surface of the single-crystal silicon carbide substrate by a mirror electron microscope.

In the case where the main surface of the single-crystal silicon carbide substrate is irradiated with an electron beam at an accelerated voltage of 5 keV or less in order to capture the image of the main surface by the mirror electron microscope, the main surface is not charged up.

A method for producing a single-crystal silicon carbide substrate in an embodiment according to the present invention includes step (A) of preparing a single-crystal silicon carbide substrate having a main surface; step (B) of processing the main surface of the single-crystal silicon carbide substrate by mechanical polishing until the main surface has a surface roughness of $Ra \leq 5$ nm; step (C) of processing the main surface, by chemical mechanical polishing after step (B); step (D) of etching the main surface after step (C); and step (E) of oxidizing the main surface at any time point between the step (C) and the step (D). In the step (C), a polishing amount t of the main surface by the chemical mechanical polishing fulfills a relationship of $Ra \times 70 \leq t$, where Ra is the surface roughness in the step (B).

The step (E) may be performed between the step (C) and the step (D); and the step (E) of oxidizing the main surface may be performed by reactive ion etching with gas containing oxygen.

The step (D) and the step (E) may be alternately performed a plurality of times.

The step (D) performed at a final time among the plurality of times may be performed with an aqueous solution containing hydrofluoric acid.

The step (E) may be performed at the same time as the step (C).

The step (E) may be performed at the seine time as the step (D).

The step (D) and the step (E) may be performed by reactive ion etching.

A method for inspecting a single-crystal silicon carbide substrate in an embodiment according to the present invention, comprises the steps of: observing a main surface of a single-crystal silicon carbide substrate by a mirror electron microscope while being irradiated with an electron beam or an electron beam and an ultraviolet ray; and determining whether the single-crystal silicon carbide substrate is good or poor based on a ratio of hidden scratches of the main surface.

The ultraviolet ray may have an energy larger than or equal to, a bandgap of a material forming the single-crystal silicon carbide substrate to be inspected.

The main surface of the single-crystal silicon carbide substrate may have a surface roughness of 0.2 nm or less.

The main surface of the single-crystal silicon carbide substrate may have an oxide layer having a thickness of 5 nm or less.

In the case where the main surface is arbitrary observed at 50 or more observation points with a field of view having a diameter of 100 μm, the ratio of hidden scratches may be defined by a value obtained by dividing the number of the observation points at which a striped hidden scratch having a length of at least 50 μm by the total number of the observation points.

The method for inspecting a single-crystal silicon carbide substrate according to the present invention evaluates a defect, which is difficult to be observed by an optical method. The present invention also provides a single-crystal silicon carbide substrate in which defects are suppressed and a method for such a single-crystal silicon carbide substrate.

DETAILED DESCRIPTION OF PREFERRED EMBODIMENTS

As a result of studying the surface of a single-crystal silicon carbide substrate in detail, the present inventors suggested the following: defects are present at the surface of the single-crystal silicon carbide substrate, which is determined as being smooth by an optical method or the like, and are also present inside the single-crystal silicon carbide substrate. The present invention suppresses generation of the defects that are not observed by a conventional method. Hereinafter, the present invention will be described in detail.

First, the present inventors attempted to confirm the presence of hidden defects at a surface of a single-crystal silicon carbide substrate, determined as being smooth by an optical method or the like, by use of a mirror electron microscope (MEM). The mirror electron microscope was used for the following reason. The mirror electron microscope visualizes an equipotential surface of an observation target, and therefore is believed by the present inventors to capture a change in the equipotential surface caused by a hidden defect. The mirror electron microscope will be described in detail later. According to the detailed studies made by the present inventors, the defects that are not observed by a conventional optical method or the like are considered to be present in an area from the surface to the inside of the single-crystal silicon carbide substrate, and are observed by the mirror electron microscope as being striped. Based on these, it has been found that the defects have different equipotential surfaces in stripes. Hereinafter, such a cause of the change in the equipotential surface will be referred to as a "hidden scratch". The hidden scratches are presumed to be parts of a strained layer (crushed layer) generated inside the substrate at the time of mechanical polishing performed on the surface of the substrate and remaining without being removed by polishing performed later, or parts generated inside the substrate by CMP or the like and having a different quality from that of the uniform material used for forming the substrate.

In this specification, the term "main surface" refers to a face on which a silicon carbide semiconductor layer is formed among a plurality of faces of the single-crystal silicon carbide substrate. The term "main surface" also refers to a conceptual face defining the single-crystal silicon carbide substrate. The term "surface" refers to an exposed area of the conceptual face. Therefore, the main surface of the single-crystal silicon carbide substrate is kept the same even after the single-crystal silicon carbide substrate is polished. By contrast, the exposed surface of the main surface is changed after the single-crystal silicon carbide substrate is polished.

According to the studies made by the present inventors, the main surface, of the single-crystal silicon carbide substrate, having hidden scratches is as flat as a plane having atoms. Therefore, the hidden scratches are not confirmed to be present by the method disclosed in Japanese Patent No. 3761546 or the optical interference-system surface roughness meter disclosed in Japanese Laid-Open Patent Publication No. 2011-220744 or Japanese Laid-Open Patent Publication No. 2008-288240; more specifically, for example, a wafer surface inspection device (e.g., Candela of KLA) usable for a common optical method.

The hidden scratches are present inside the substrate, and therefore, are generally considered as being difficult to be detected by non-destructive inspection. For example, it has been reported that the defects inside a GaN substrate are observed by use of cathode luminescence (e.g., Japanese Laid-Open Patent Publication No. 2010-254576). However, the GaN substrate is formed of a direct bandgap semiconductor. The silicon carbide substrate, which is formed of an indirect bandgap semiconductor, cannot be inspected by substantially the same method. In the case where, as in Japanese Laid-Open Patent Publication No. 2008-166329, destructive inspection is used to detect the defects, observation is performed by a high resolution method. Therefore, the field of view is narrow and it is difficult to observe a large area of the substrate.

In view of such problems, the present inventors conceived using a mirror electron microscope to observe the hidden scratches in the single-crystal silicon carbide substrate. The present inventors also conceived evaluating the single-crystal silicon carbide substrate based on the density of the hidden scratches observed by the mirror electron microscope, and also a method for producing a high quality single-crystal silicon carbide substrate with few hidden scratches.

Hereinafter, a single-crystal silicon carbide substrate, a method for producing the single-crystal silicon carbide substrate, and a method for inspecting the single-crystal silicon carbide substrate in an embodiment will be described with reference to the drawings.

(Mirror Electron Microscope)

Figure 1:
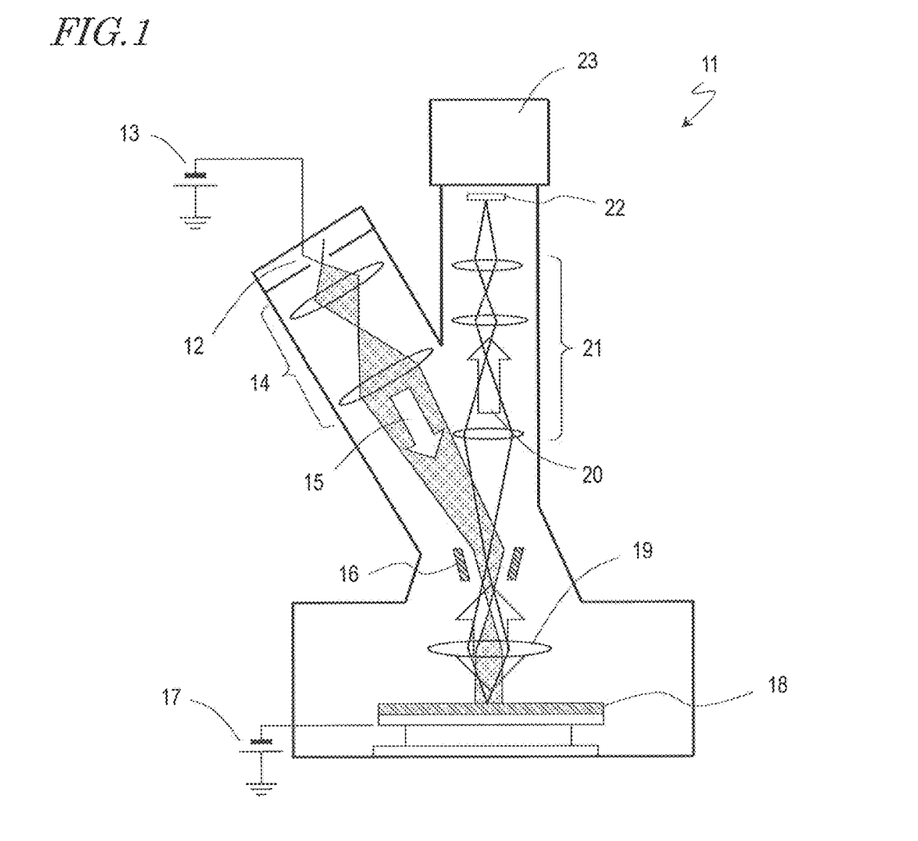
FIG. 1 is a schematic view showing a structure of a mirror electron microscope.

First, a mirror electron microscope will be described. The mirror electron microscope is explained in, for example, Hitachi Review, February 2012 issue, pages 46-51. The mirror electron microscope is a type of electron microscope. An electron beam directed toward a sample is decelerated and inverted immediately before the sample, and the returned beam is focused to form an image by an electron lens to allow a surface state of the sample to be observed. FIG. 1 schematically shows a structure of such a mirror electron microscope. As shown in FIG. 1, a mirror electron microscope 11 includes an electron source 12, a first electron lens 14, a separator 16, a second electron lens 21, a fluorescent plate 22, and an image capturing device 23.

The electron source 12 is connected with a power source 13, and emits an electron beam 15. The electron beam 15 is converged by the first electron lens 14, passes the separator 16, and advances toward a surface of a sample 18.

The sample 18 is electrically insulated from, and is supported on, a stage. The sample 18 is provided with a negative potential by a power source 17. Because of the negative potential provided to the sample 18, the electron beam 15 is inverted in the vicinity of the surface of the sample 18 without colliding against the sample 18 and advances away from the sample 18.

The electron beam returning from the sample 18 (such an electron beam is referred to as the "electron beam 20") passes the separator 16 and is converged by the second electron lens 21. The separator 16 separates an optical path for the electron beam 15 advancing toward the sample 18 and an optical path for the electron beam 20 returning from the sample 18 from each other. As a result, an image is formed at a surface of the fluorescent plate 22. The image capturing device 23 captures the image formed at the fluorescent plate 22.

As described above, the mirror electron microscope 11 uses the electron beam inverted at the surface of the sample 18. Therefore, an image of a shape reflecting the electrostatic potential in the vicinity of the surface of the sample 18 and also an image of a shape reflecting the distribution of electrons in an area from the surface to the inside of the sample 18 are formed.

Figure 2A:
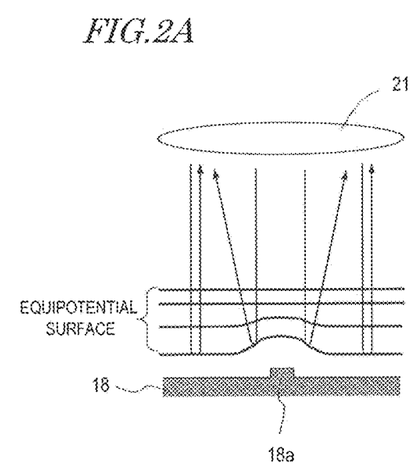
FIG. 2A and FIG. 2B each schematically show a sample to be observed by the mirror electron microscope as well as the electrostatic potential distribution and inversion of an electron beam.
Figure 2B:
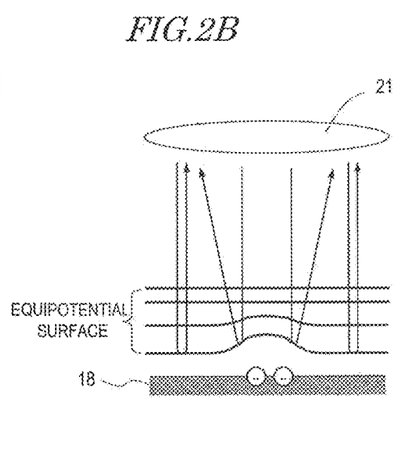

FIG. 2 and FIG. 3 each schematically show a surface shape of the sample 18 and the distribution of electrons inside the sample 18 as observed by the mirror electron microscope, as well as the electron beam influenced by the surface shape and the distribution of electrons. In FIG. 2A, a convexed portion 18a is present at the surface of the sample 18. In this case, the equipotential surface at the surface of the sample 18 protrudes at the convexed portion 18a. The electron beam is considered to be scattered as expanding at the protruding portion of the equipotential surface. In FIG. 2B, the surface of the sample 18 is flat but negative charges are locally present in the vicinity of the surface of the sample 18. In this case, similar to the case of FIG. 2A, the electron beam is scattered as expanding at the portion where the negative charges are locally present. In this case, a portion of the image formed by the second electron lens 21 that corresponds to the portion where the electron beam is scattered is darker than the rest of the image.

Figure 3A:
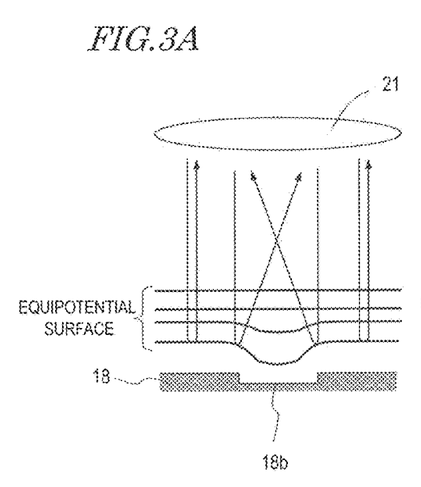
FIG. 3A and FIG. 3B each schematically show a sample to be observed by the mirror electron microscope as well as the electrostatic potential distribution and inversion of an electron beam.
Figure 3B:
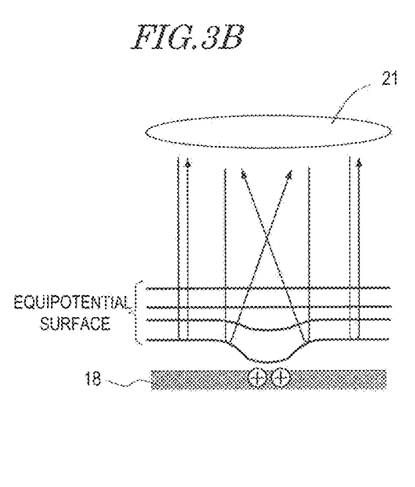

In FIG. 3A, a concaved portion 18b is present at the surface of the sample 18. In this case, the equipotential surface at the surface of the sample 18 is recessed at the concaved portion 18b. The electron beam is considered to be converged at the recessed portion of the equipotential surface. In FIG. 3B, the surface of the sample 18 is flat but positive charges are locally present in the vicinity of the surface of the sample 18. In this case, similar to the case of FIG. 3A, the electron beam is converged at the portion where the positive charges are locally present. In this case, a portion of the image formed by the second electron lens 21 that corresponds to the portion where the electron beam is converged is brighter than the rest of the image.

As described above, in the case where the sample 18 is observed by the mirror electron microscope, the sample 18 is biased to a negative potential. Therefore, in the case where a single-crystal silicon carbide substrate is used as the sample 18, if the substrate has hidden scratches, charges are locally present at the hidden scratches in relation to the negative potential at the surface of the sample 18. For this reason, even if the surface of the single-crystal silicon carbide substrate is flat, an image of the hidden scratches inside the substrate is captured and thus the hidden scratches are observed.

The sample is observed by the mirror electron microscope based on the above-described principle. Therefore, especially in the case where the surface of the sample is highly insulating, the sample may possibly be charge up. Even in this case, the charge-up, namely, the accumulation of the electrons in the sample, may reflect, to some extent, the surface shape of the sample or the uniformity of materials inside the sample. However, in the case where the amount of the accumulated electrons is excessively large, the microscopic surface shape, or the distribution of materials inside the sample that are to be observed, may not possibly be reflected on the equipotential surface. In such a case, it is preferably to remove the charge-up of the sample.

Now, it is assumed that the sample is a single-crystal silicon carbide substrate. When, for example, the single-crystal silicon carbide substrate is irradiated with an ultraviolet ray having an energy larger than, or equal to, the bandgap of silicon carbide (3.2 eV) forming the substrate, hole-electron pairs are generated in the substrate. The generated holes, when being bonded with the electrons, decrease the electrons, which causes the charge-up. In addition, the ultraviolet ray invades the inside of the single-crystal silicon carbide substrate to some extent. For example, an ultraviolet ray having a wavelength of 365 nm (energy: 3.4 eV) invades the inside of the single-crystal silicon carbide substrate to a depth of about 120 μm. The electrons of the generated hole-electron pairs are considered to be trapped in the hidden scratches inside the single-crystal silicon carbide substrate as a result of the invasion. Therefore, in the case where the single-crystal silicon carbide substrate is observed by the mirror electron microscope while being irradiated with the ultraviolet ray, even when an electron beam is directed toward a main surface of the single-crystal silicon carbide substrate at an accelerated voltage of 5 keV or less, the charge-up is suppressed and the contrast of the hidden scratches in the captured image is increased. Thus, the hidden scratches are made easier to observe.

As described above, in the case where the main surface of the single-crystal silicon carbide substrate is observed by the mirror electron microscope, the captured image shows hidden scratches that are shown brighter or darker than the rest. Detailed studies made by the present inventors have found that such hidden scratches are generated in the mechanical polishing step and the CMP step performed during the production of the single-crystal silicon carbide substrate.

As can be seen from the above, for producing a single-crystal silicon carbide substrate, generation of hidden scratches is prevented as much as possible, and the hidden scratches, if generated, are removed as much as possible. In this manner, a single-crystal silicon carbide substrate which has few hidden scratches and allows a high quality silicon carbide semiconductor layer to be formed thereon is produced.

(Method for Producing a Single-Crystal Silicon Carbide Substrate)

Hereinafter, a method for producing a single-crystal silicon carbide substrate in an embodiment will be described in detail.

Figure 4A:
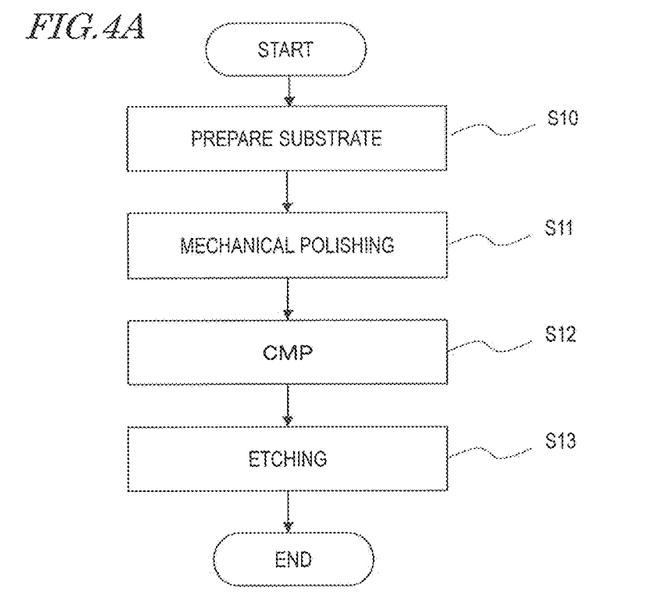
FIG. 4A is a flowchart showing a method for producing a single-crystal silicon carbide substrate in an embodiment.

FIG. 4A is a flowchart showing one method for producing a single-crystal silicon carbide substrate according to the present invention. FIG. 5A through FIG. 5D, FIG. 5E and FIG. 5F are cross-sectional views showing steps of the method for producing the single-crystal silicon carbide substrate.

Figure 5A:
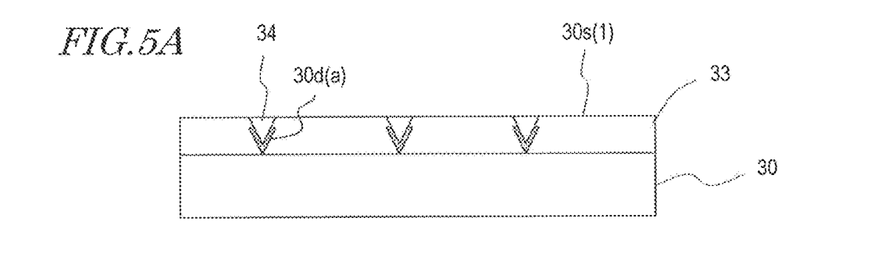
FIG. 5A through FIG. 5D, FIG. 5E and FIG. 5F are cross-sectional showing steps of the method for producing the single-crystal silicon carbide substrate in the embodiment.

First, in step S10, as shown in FIG. 5A, a single-crystal silicon carbide substrate 30 having a main surface 30s is prepared. The single-crystal silicon carbide substrate 30 is obtained by slicing a part of a single crystalline silicon carbide ingot of a desired polytype such that the main surface 30s has a desired crystal orientation. There is no specific limitation on the thickness, the size or the crystal orientation of the single-crystal silicon carbide substrate 30. The thickness, the size and the crystal orientation suitable to the use may be selected. For example, the single-crystal silicon carbide substrate 30 has a thickness of 200 μm or greater and 600 μm or less, and a diameter of 2 inches or greater and 8 inches or less. The crystal orientation of the main surface 30s may be, for example, (0001), (000-1) or the like in the case where the silicon carbide is of hexagonal crystal, and may be (111) or the like in the case where the silicon carbide is of cubic crystal. The main surface 30s may be inclined from such an orientation at an angle of 0 degrees or greater and 1 degree or less. As shown in FIG. 5A, a strained layer (processing-denatured layer) 33 is formed at the main surface 30s of the single-crystal silicon carbide substrate 30. The strained layer 33 is generated at the time of slicing of the single crystalline silicon carbide ingot.

Next, in step S11, the main surface 30s of the prepared single-crystal silicon carbide substrate 30 is processed by mechanical polishing. The mechanical polishing is performed by use of, for example, an abrasive grain of diamond or the like and a device such as a polisher, a grinder or the like.

Figure 5B:
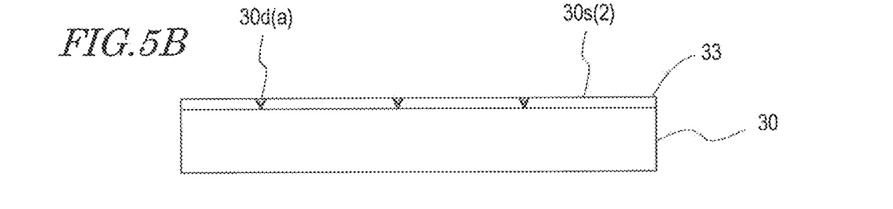

The mechanical polishing gradually decreases the surface roughness of a surface 30s(1) of the main surface 30s. As a result, as shown in FIG. 5B, the strained layer 33 located at the main surface 30s has a thickness thereof decreased. However, the abrasive grain used for the mechanical polishing newly generates a strained layer at scratches 34 or at a level deeper than the scratches 34. Such a strained layer becomes hidden scratches 30d(a). The density of the hidden scratches 30d(a) depends on the depth of the scratches 34, namely, the roughness of the surface 30s(1) of the main surface 30s. Therefore, the post-mechanical polishing roughness of the surface of the main surface 30s (i.e., surface 30s(2)) is preferably as small as possible. Specifically, the post-mechanical polishing roughness Ra of the surface 30s(2) of the main surface 30s is preferably Ra≤about 5 nm. In this manner, the roughness of the surface of the main surface may be decreased as much as possible by mechanical polishing, so that the density of the hidden scratches 30d(a) is decreased. Therefore, the post-mechanical polishing roughness Ra of the surface 30s(2) is more preferably Ra≤3 nm and especially preferably Ra≤1 nm. The minimum roughness of the surface of the main surface that is achievable by the mechanical polishing is Ra≥about 0.3 nm. In consideration of the cost of the mechanical polishing, it is preferable that Ra≥about 0.5 nm.

Next, in step S12, the main surface 30s is processed by chemical mechanical polishing (CMP). The CMP is performed by use of a polishing slurry containing a dispersion medium and an abrasive grain dispersed in the dispersion medium.

The roughness Ra of the main surface may be measured by, for example, an atomic force microscope (AFM). Specifically, Nanoscope 3A of Digital Instruments is usable.

The abrasive grain contained in the polishing slurry may be of silicon oxide, aluminum oxide, cerium oxide, titanium oxide or the like. Among these substances, a silicon oxide abrasive grain such as colloidal silica, fumed silica or the like, which is easily dispersed uniformly in a liquid, is preferable. As the dispersion medium, water is generally used.

Figure 5C:
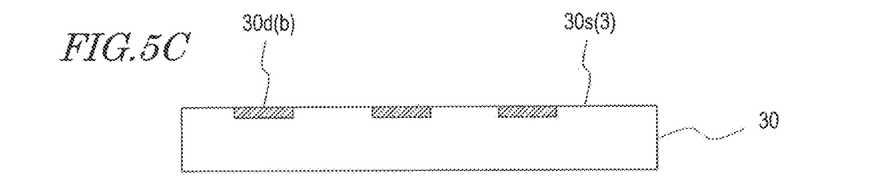

As shown in FIG. 5C, the strained layer 33 is removed almost completely by the CMP step. The hidden scratches 30d(a) are also removed. However, as a result of the CMP step, hidden scratches 30d(b) of a composite oxide containing silicon, carbon and oxygen are generated at a surface 30s(3) of the main surface 30s.

A processing amount t in the CMP step preferably fulfills Ra×70≤t. Ra is the post-mechanical polishing roughness of the surface 30s(2) of the main surface 30s described above. In the case where the processing amount t fulfills the above-mentioned relationship, the strained lever 33 is removed almost completely. The processing performed by the CMP step is costly. Therefore, it is preferable that the processing amount t is smaller than maximum diameter D of the abrasive grain used for the mechanical polishing step performed immediately before the CMP step; namely, it is preferable that the processing amount t fulfills t≤D. More preferably, the processing amount t fulfills Ra×200≤t≤D, and still more preferably, the processing amount t fulfills Ra×1000≤t≤D.

Next, in step S13, the surface 30s(3) of the main surface 30s processed by the chemical mechanical polishing is etched. As a result of the etching, silicon carbide is removed to a predetermined depth from the surface 30s(3) of the main surface 30s, and thus the hidden scratches 30d(b) generated by the CMP step are removed. In this manner, the single-crystal silicon carbide substrate in which the hidden scratches 30d(a) and the hidden scratches 30d(b) are decreased is obtained.

The etching may be performed by gas phase etching. In this case, for example, ion etching, reactive ion etching (hereinafter, may be referred to simply as "RIE"), plasma etching, reactive ion beam etching, ion beam etching or the like is usable.

There is no specific limitation on the type of gas usable for the gas phase etching. It is preferable to use gas reactive with silicon carbide, for example, fluorine-containing gas such as carbon tetrafluoride gas, sulfur hexafluoride gas or the like, or hydrogen.

Etching conditions such as a power to be applied or the like are determined based on, for example, the device used for the etching. The etching rate preferably does not exceed 10 μm/h. An etching rate exceeding 10 μm/h is excessive for the main surface 30s of the single-crystal silicon carbide substrate 30, which may undesirably damage the main surface 30s because ions collide against the main surface 30s or may undesirably deteriorate the post-etching surface morphology of the main surface 30s.

The etching may also be performed by liquid phase etching. In this case, for example, an aqueous solution containing hydrofluoric acid is usable. Specifically, hydrofluoric acid, buffered hydrofluoric acid (BHF), fluonitric acid or the like is usable.

Regardless of whether the etching is performed by gas phase etching or liquid phase etching, the single-crystal silicon carbide substrate 30 may be rinsed with pure water after step S13.

Figure 5D:
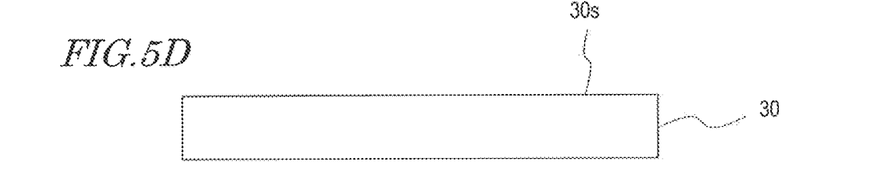

With the method for producing the single-crystal silicon carbide substrate in this embodiment, it is preferable to remove, as much as possible in the etching step, the hidden scratches 30d(b), which are generated by partial oxidation of single crystalline silicon carbide. For this purpose, it is preferable that the etching step, the single-crystal silicon carbide substrate is etched, for example, by a thickness (to a depth) of 20 nm or greater and 500 nm or less from the surface from the surface 30s(3) of the main surface 30s. As a result, the hidden scratches 30d(b) are removed, together with a part of the substrate, from the main surface 30s of the single-crystal silicon carbide substrate 30. Thus, as shown in FIG. 5D the single-crystal silicon carbide substrate 30 having few hidden scratches is obtained.

With the method for producing the single-crystal silicon carbide substrate in this embodiment, in order to efficiently remove the hidden scratches 30d(a) and the hidden scratches 30d(b), the surface 30s(2) or 30s(3) of the main surface 30s may be oxidized at any time point between the CMP step S12 and the etching step S13. The expression "at any time point between the CMP step S12 and the etching step S13" refers to: at time same time as the CMP step S12, at the same time as the etching step S15, or between the CMP step S12 and the etching step S13. At such a time point, the surface 30s(2) or 30s(3) of the main surface 30s may be oxidized.

First, an example in which the CMP step (step S12) or the etching step (step S13) is performed while the surface 30s(2) or 30s(3) is oxidized will be described.

Figure 4B:
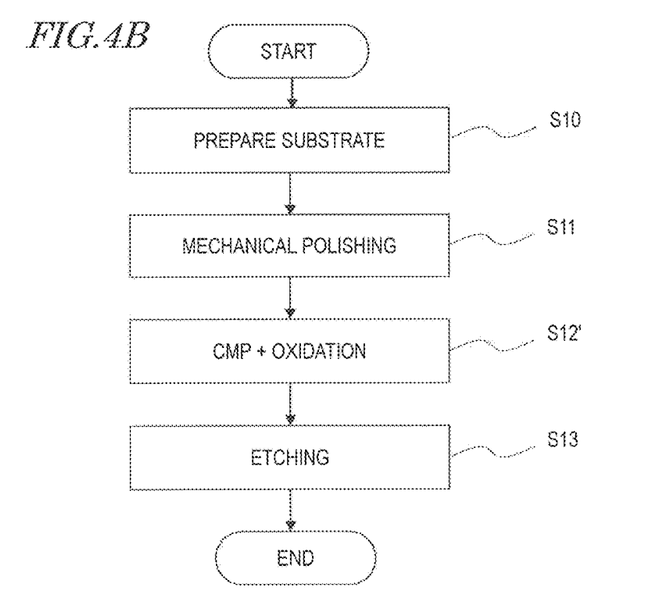
FIG. 4B is a flowchart showing another method for producing a single-crystal silicon carbide substrate in an embodiment.
Figure 5E:
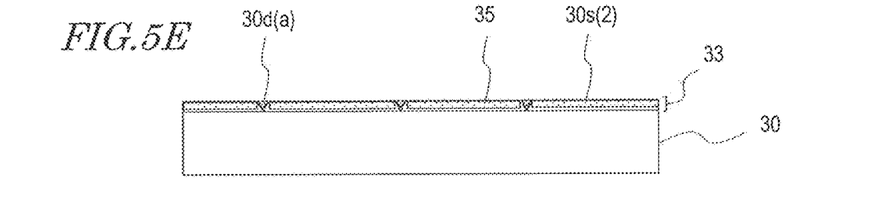

As shown in, for example, FIG. 4B, after the mechanical polishing step (S11), the CMP and the oxidation may be performed at the same time in step S12'. For this purpose, the polishing slurry may further contain an oxidizer. Namely, the dispersion medium may have the oxidizer dispersed therein. The oxidizer may contain, for example, at least one selected from the group consisting of hydrogen peroxide, ozone, permanganate, peracetic acid, perchlorate, periodic acid, periodate, and hypochlorite. The oxidizer also oxidizes the strained layer 33 during the CMP step. Specifically, as shown in FIG. 5E, the surface 30s(2) of the main surface 30s is oxidized during the CMP step to form an oxide layer 35 in the strained layer 33. This increases the etching rate for the strained layer 33 during the CMP step, and thus the hidden scratches 30d(a) are removed more certainly.

Figure 4C:
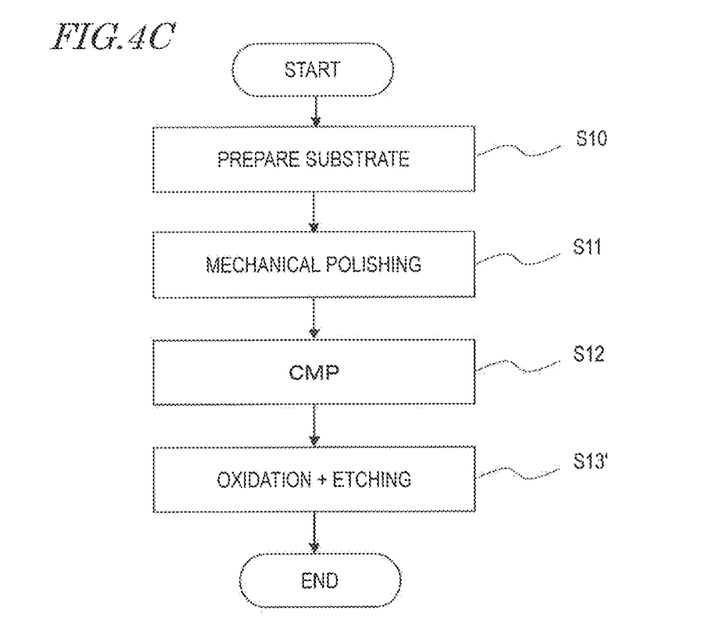
FIG. 4C is a flowchart showing still another method for producing a single-crystal silicon carbide substrate in an embodiment.
Figure 5F:
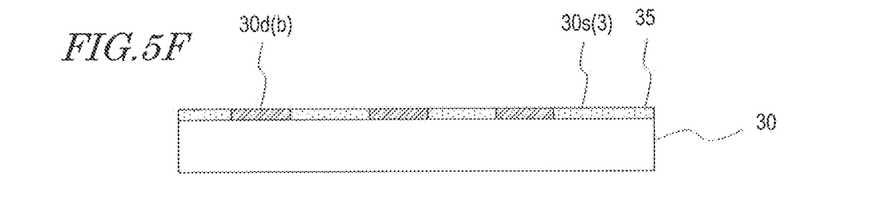

As shown in FIG. 4C, after the CMP step (S12), the etching and the oxidation may be performed at the same time in step S13'. For this purpose, the etching may be performed in an oxidized atmosphere. In the case where the etching in step S13' is performed by gas phase etching, any of the above-mentioned types of gas that contains oxygen may be used. In the case where the etching in step S13' performed by liquid phase etching, an oxidizer such as hydrogen peroxide, sulfuric acid, hydrochloric acid or the like may be incorporated into any of the above-mentioned etchants. As a result, as shown in FIG. 5F, at the surface 30s(3) having the hidden scratches 30d(b), silicon carbide is oxidized into an oxide of silicon to form the oxide layer 35. Since the oxide layer 35 contains a large amount of oxygen and contains carbon and silicon in an oxidized state, the surface 30s(3) is made easily etchable. This increases the etching rate in the etching step, and thus the hidden scratches 30d(b) are removed more certainly.

Figure 4D:
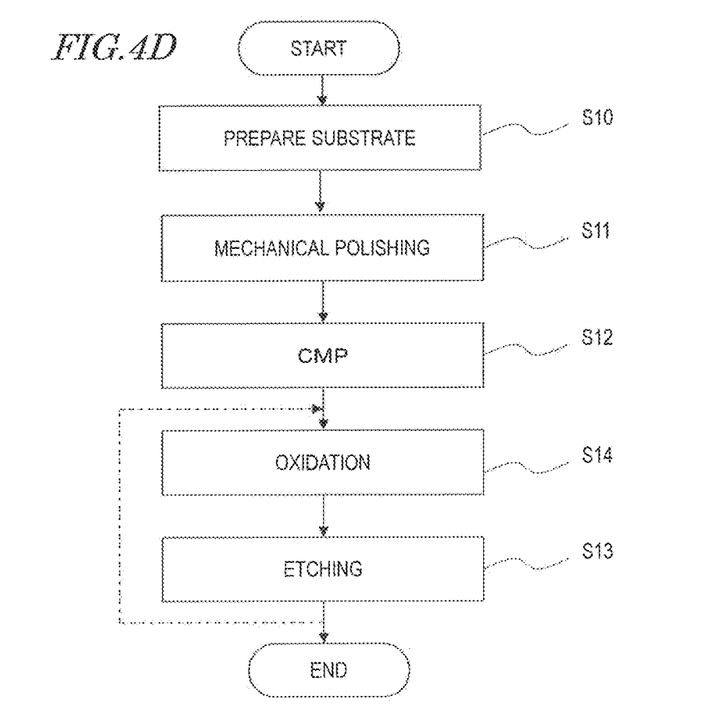
FIG. 4D is a flowchart showing still another method for producing a single-crystal silicon carbide substrate in an embodiment.

In order to remove the hidden scratches 30d(b) more certainly in the etching step, as shown in FIG. 4D, an oxidation step S14 may be performed between the CMP step S12 and the etching step S13.

For example, the surface 30s(3) of the main surface 30s is oxidized in gas phase to form an oxide. In this step, silicon carbide containing the hidden scratches 30d(b) is oxidized in gas phase. As shown in FIG. 5F, the oxide layer 35 is formed at the main surface 30s. For the oxidation step S14, any of wet oxidation, anodic oxidation, plasma oxidation, thermal oxidation and ozone oxidation is usable.

In the case where the oxidation step S14 is performed by use of plasma oxidation, surface 30s(3) of the main surface 30s of the single-crystal silicon carbide substrate 30 may be exposed to oxygen plasma by, for example, reactive ion etching to form the oxide layer 35. For example, the plasma oxidation is performed at a pressure of about $10^{-1}$ to $10^2$ Pa and a power of about 0.01 to 2 W/cm$^2$ in an oxygen atmosphere or in an atmosphere containing oxygen and inert gas such as Ar or the like. In the case where the etching step S13 following the oxidation step S14 is performed by reactive ion etching, the plasma oxidation is preferably performed in the same device as used for the reactive ion etching. A reason for this is that the two steps are performed continuously with merely the gas being exchanged with no need to transfer the single-crystal silicon carbide substrate 30.

In the case where the oxidation step S14 is performed by thermal oxidation, the oxide layer 35 is formed while the single-crystal silicon carbide substrate 30 is kept at a high temperature in an oxygen atmosphere. For example, the single-crystal silicon carbide substrate 30 is kept at a temperature of 900° C. to 1500° C. for 10 to 240 minutes in an oxygen atmosphere.

In the case where the oxidation step S14 is performed by ozone oxidation, the surface 30s(3) of the main surface 30s of the single-crystal silicon carbide substrate 30 is exposed to ozone. For example, the single-crystal silicon carbide substrate 30 is irradiated with an ultraviolet ray for 1 to 60 minutes in an ozone gas stream.

In the case where the oxidation step S14 is performed, the etching step S13 following the oxidation step S14 mainly removes the generated oxide layer 35. A part of silicon carbide is oxidized to form the oxide layer 35, and the oxide layer 35 is mainly formed of silicon carbide from a microscopic point of view. The etching step S13 following the oxidation step S14 etches the oxide layer 35 in a milder condition than the etching step S13 in the case where the oxidation step S14 is not performed.

In the case where the oxidation step S14 is performed, the oxidation step S14 and the etching step S13 may be alternately performed a plurality of times. This allows the oxidation step S14 to be performed in a milder condition. Depending on the condition under which the oxidation step S14 is performed, the possibility that the single-crystal silicon carbide substrate 30 is damaged may be reduced, the temperature in the oxidation step S14 may be decreased, or the output needed to generate the plasma may be decreased.

In the case where the oxidation step S14 and the etching step S13 are alternately performed a plurality of times, the final etching step S13 is preferably performed with an aqueous solution containing hydrofluoric acid. This allows the oxide to be removed from the surface 30s(3) of the main surface 30s to finish the single-crystal silicon carbide substrate 30 without damaging the single crystalline silicon carbide substrate 30.

In order to efficiently remove both of the hidden scratches 30d(a) generated by the mechanical polishing step and the hidden scratches 30d(b) generated by the CMP step, the oxidation step may be performed at the same time as the CMP step and also at the same time as the etching step following the CMP step. As shown in, for example, FIG. 4E, after the mechanical polishing step (S11), CMP and oxidation are performed at the same time (S12') as described above. After this, in step S13-1, etching is performed in gas phase or liquid phase. Next, in step S13', etching and oxidation are performed at the same time. Then, in step S13-2, etching is performed again in gas phase or liquid phase. One of, or both of the steps S13-1 and S13-2, may be omitted. Such a method efficiently removes the hidden scratches 30d(a) and 30d(b) as described above, and thus increases the productivity of the single-crystal silicon carbide substrate 30.

(Method for Inspecting the Single-Crystal Silicon Carbide Substrate and the Single-Crystal Silicon Carbide Substrate in this Embodiment)

Now a method for inspecting a single-crystal silicon carbide substrate in this embodiment will be described. The method for inspecting a single-crystal silicon carbide substrate in this embodiment is as follows. A single-crystal silicon carbide substrate having a polished main surface is observed by a mirror electron microscope while being irradiated with an electron beam or with an electron beam and an ultraviolet ray. Based on the ratio of hidden scratches at the main surface, it is determined whether the single-crystal silicon carbide substrate is good or poor. A conventional method for inspecting a single-crystal silicon carbide substrate does not detect a hidden scratch in a non-destructive manner. By contrast, the method in this embodiment evaluates whether there is a hidden scratch or not. The ratio of hidden scratches is controlled, so that it is determined whether the single-crystal silicon carbide substrate is of a high quality or not.

For observing the main surface by the mirror electron microscope, it is preferable that the main surface is irradiated with an ultraviolet ray as described above. This suppresses the charge-up of the single-crystal silicon carbide substrate and thus allows the hidden scratches to be observed more certainly.

In an example of inspection method, the ratio of hidden scratches in the entire plane of the main surface may be used for the evaluation. The "ratio of hidden scratches" is defined as follows. Observation points are set at a predetermined interval at the main surface of the single-crystal silicon carbide substrate. The number of the observation points at which the presence of the hidden scratch is confirmed is divided by the total number of the observation points. The resultant value is the "ratio of hidden scratches". The field of view of the mirror electron microscope at an observation point is, for example, a circle having a diameter of 100 μm or greater and 200 μm or less. The observation points are set at an interval of, for example, 200 μm or greater and less than, or equal to, the radius of the substrate. It is now assumed that a border is set at the middle between two adjacent observation points and an area centering around each observation point is defined as an observation area. In this case, the size of the field of view of the mirror electron microscope with respect to the observation area is preferably 0.0001% or greater and 100% or less.

According to this inspection method, in the case where one striped lattice scratch is present over a plurality of observation points, it is evaluated that the plurality of observation areas include the hidden scratch. Therefore, the number of the hidden scratches and also the length and size of the hidden scratches are put into consideration to determine whether the single-crystal silicon carbide substrate good or poor. In the case where ratio of lattice scratches evaluated by this inspection method is less than 50%, SBD (Schottky Barrier Diode) elements produced by a semiconductor process including epitaxial growth in a post step may be produced at an average yield of about 80%, which is adequate. In the case where a MOS FET (Metal Oxide Semiconductor Field Effect Transistor) element, which is more influenced by the surface of the single-crystal silicon carbide substrate than the SBD element, is to be produced, the ratio of hidden scratches defined above is preferably less than 10% and more preferably 0%. In she case of the SBD element also, the ratio of hidden scratches is preferably less than 10% in order to increase the yield.

As can be seen from the above, as a result of using the inspection method in this embodiment, a single-crystal silicon carbide substrate in which the number of the processing-derived hidden scratches is decreased in a non-destructive manner and which allows a high quality silicon carbide semiconductor layer to be epitaxially grown thereon is selected. A single-crystal silicon carbide substrate having a decreased number of hidden scratches, which are not easily detected by an optical microscope or the like, and allowing a high quality silicon carbide semiconductor layer to be epitaxially grown thereon is obtained.

With the inspection method in this embodiment, the "hidden scratch" is defined as having a length that is at least ½ of the diameter of a circle defining the field of view of the mirror electron microscope and as being striped. As described above, a conceivable reason why the hidden scratch is striped is that the hidden scratch is derived from a scratch made by the mechanical polishing. The criterion based on which a scratch is detected as a hidden scratch is that the hidden scratch has a length that is at least ½ of the diameter of the field of view. Because of this criterion, for example, a scratch is evaluated as a hidden scratch relatively easily, and the evaluation is made at high reproducibility. Specifically, in the case where the diameter of the circle defining the field of view of the mirror electronic microscope is 100 μm, the number of observation points at which the presence of a striped scratch having a length of at least 50 μm is confirmed is found.

In the case where the surface roughness of the main surface of the single-crystal silicon carbide substrate is large, especially in the case where there are convexed and concaved portions that are not hidden scratches and are observable by an optical method, the hidden scratches may not be easily observed because the image is influenced by the surface roughness. In the case where a thick oxide layer having a thickness exceeding 5 nm is formed at the main surface, the hidden scratches may not be easily observed by charge-up even when the main surface is irradiated with an ultraviolet ray. Therefore, in the case where the density of the hidden scratches is evaluated by use of the mirror electron microscope, it is preferable that the surface roughness Ra of the main surface of the single-crystal silicon carbide substrate is 1 nm or less and that the maximum height Rmax thereof is 10 nm or less. Especially, the surface roughness Ra is preferably 0.2 nm. The thickness of the oxide layer formed at the main surface is preferably 5 nm or less. The maximum height Rmax may be measured by, for example, an AFM like the surface roughness Ra.

As described in the following examples, a single-crystal silicon carbide substrate produced by the production method in this embodiment may fulfill these conditions. It is now assumed that, for example, specific production conditions or the like are determined based on the method for producing a single-crystal silicon carbide substrate in this embodiment, and that the single-crystal silicon carbide substrate produced under the determined conditions is confirmed by the inspection method in this embodiment to fulfill the criterion that the ratio of hidden scratches is less than 50%. In this case, any single-crystal silicon carbide substrate produced under the determined conditions is determined as having a ratio of hidden scratches of less than 50%, even without being inspected by the inspection method in this embodiment. Namely, a single-crystal silicon carbide substrate in this embodiment is not limited to a single-crystal silicon carbide substrate confirmed by the inspection method in this embodiment as having a ratio of hidden scratches of less than 50%.

Example 1

A single-crystal silicon carbide substrate was produced by the production method in this embodiment, and the hidden scratches were observed by the mirror electron microscope. The results will be described.

Figure 4E:
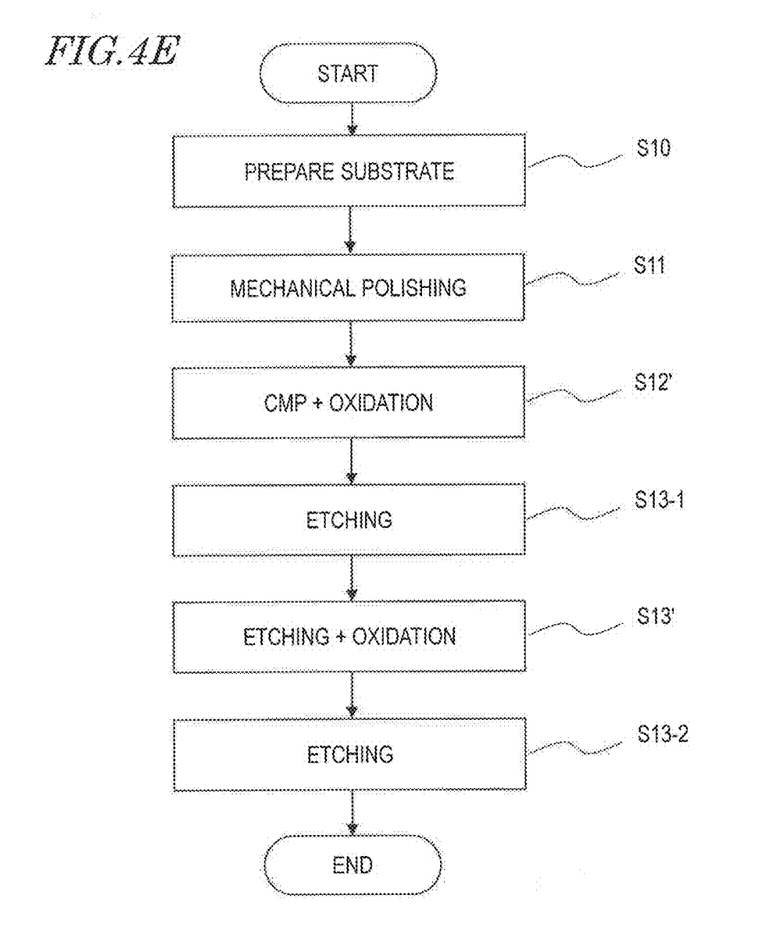
FIG. 4E is a flowchart showing still another method for producing a single-crystal silicon carbide substrate in an embodiment.

A single-crystal silicon carbide substrate was produced by the procedure shown in FIG. 4E. First, a single crystalline silicon carbide ingot was cut to obtain a substrate having an appropriate thickness (S10, step (A)). An appropriate abrasive grain was selected based on the roughness of the cut surface of the substrate, and the main surface of the substrate was processed to be flat by mechanical polishing or the like (S11, step (B)). For example, a diamond abrasive grain having a center grain diameter of 5 μm was used to polish the main surface such that the surface roughness Ra would be Ra<10 nm. Then, a diamond abrasive grain having a maximum grain diameter of 1 μm and a metal surface plate were used to polish the main surface such that the surface roughness Ra would be Ra<1 nm.

Next, the main surface was processed by CMP such that the surface roughness Ra would be Ra<0.2 nm, at a polishing amount of 1 μm by use of a slurry containing a main component of colloidal silica and also containing an oxidizer and a polishing pad (S12', steps (C) and (E)). In this manner, the oxidation step and the CMP step were performed at the same time. After CMP was finished, the substrate was washed with a solution containing HF (S13-1, step (D)). Then, the main surface was etched by 20 nm by RIE using oxygen and RIE using $CF_4$. In this manner, the oxidation step by RIE using oxygen and the etching step were performed at the same time (S13' steps (D) and (E)), and also the etching step by RIE using $CF_4$ was performed. These steps were repeated. Next, the main surface of the substrate was etched with a solution containing HF (S13-2, step (D)), and then was rinsed with pure water. Another surface, which is not the main surface, may have a large Ra for releasing heat or may be a second main surface for epitaxial growth. This may be determined in accordance with the purpose. In the case where the another surface is the second main surface, after the first main surface is processed by the CMP step, the oxidation step and the etching step, the second main surface may processed in the same manner with the first main surface being masked with a resist.

For a comparison, a main surface of another single-crystal silicon carbide substrate was entirely processed in accordance with the method shown in FIG. 4E up to the CMP step S12'. Before the etching step S13-1, a part of the main surface was covered with a resist so as not to be processed with the etching steps S13-1, S13' and S13-2.

The observation with the mirror electron microscope was performed at an accelerated voltage of 5 keV, and in the presence and the absence of irradiation with an ultraviolet ray having a wavelength of 365 nm.

Figure 6A:
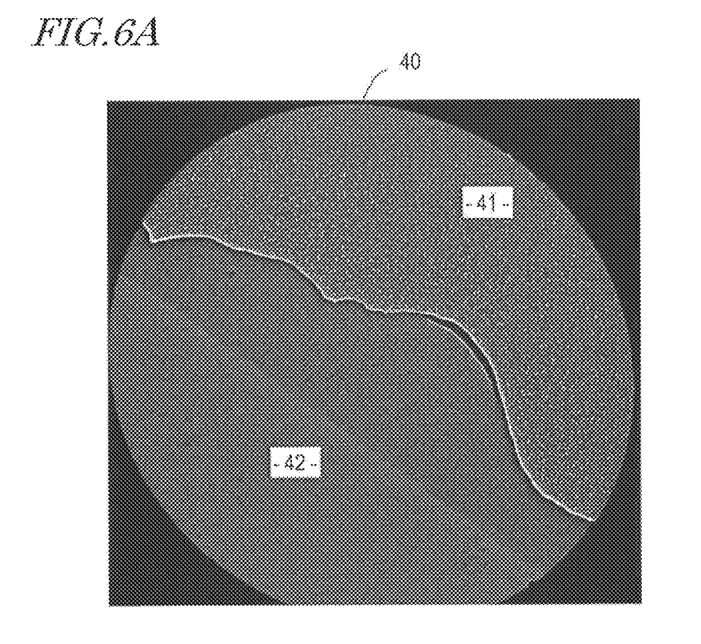
FIG. 6A shows an example of image captured by the mirror electron microscope in the case where irradiation with an ultraviolet ray is not performed.
Figure 6B:
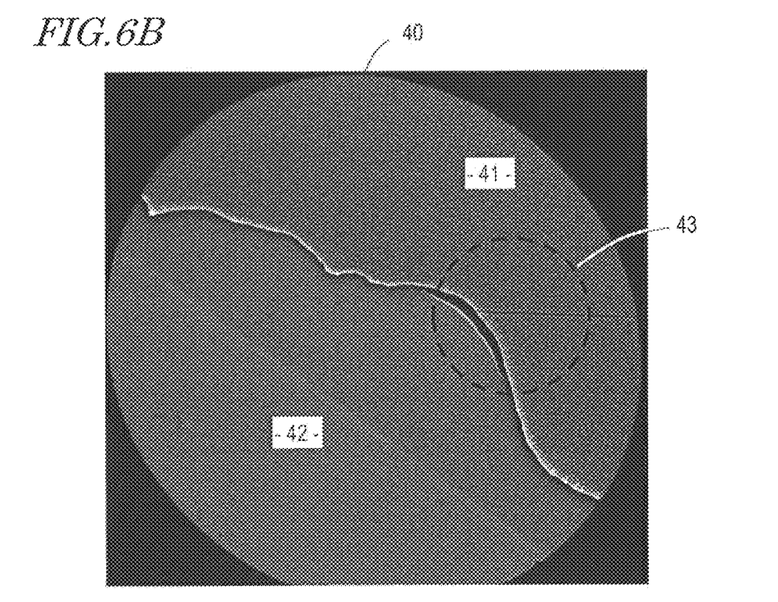
FIG. 6B shows an example of image captured by the mirror electron microscope in the case where irradiation with an ultraviolet ray is performed.

FIG. 6A and FIG. 6B each show a part of an image obtained by the mirror electron microscope. In FIG. 6A and FIG. 6(b), an area 40 is a circular observation area having a diameter of 100 μm. In the area 40, a top right part 41 was not processed by the etching steps S13, and a bottom left part 42 was processed by all the steps in the production method in this embodiment. The image in FIG. 6A was captured with no irradiation of the ultraviolet ray, whereas the image in FIG. 6(b) was captured with irradiation of the ultraviolet ray having a wavelength of 365 nm.

As shown in FIG. 6A, the part 41 of the area 40 shows white dots. This shows that the sample is charged up. By contrast, the part 42 of the area 40 does not show any white dot. Neither the part 41 nor the part 42 shows any striped portion.

As shown in FIG. 6B, in the image captured with irradiation of the ultraviolet ray, the part 41 does not show any white dot. However, an area 43 enclosed by dashed circle shows a black striped portion. This is considered to be a hidden scratch. The part 42 does not show any striped portion, like in the part 42 in FIG. 6A.

As described above, in the single-crystal silicon carbide substrate produced by the production method in this embodiment, no striped hidden scratch was observed in the observation area. From this, it is seen that in this embodiment, a single-crystal silicon carbide substrate having few hidden scratches and allowing a quality silicon carbide semiconductor layer that has low defect density to be formed thereon is obtained. It is also seen that the method for inspecting a single-crystal silicon carbide substrate in this embodiment allows the hidden scratches to be observed and allows the quality of the single-crystal silicon carbide substrate to be evaluated based on the density of the hidden scratches.

Example 2

Samples of single-crystal silicon carbide substrate in examples A through E and comparative examples A through F were produced. For producing these samples, the post-mechanical polishing surface roughness Ra and the CMP polishing amount t were different. The etching with $CF_4$ in RIE (removal step) was performed for some samples and was not performed for the other samples, and the etching with $O_2$ (oxidation step) was performed for some samples and was not performed for the other samples. The production conditions are shown in Table 1. The other conditions were the same as those in example 1.

The ratio of hidden scratches was found for the produced single-crystal silicon carbide substrates in examples A through E and comparative examples A through F. From each single-crystal silicon carbide substrate having a diameter of 100 mm, a peripheral area having a width of 2 mm was removed, and the rest was set as an effective area. In the effective area, 85 observation points were set.

The mirror electron microscope was used to capture an image of the main surface of each single-crystal silicon carbide substrate at each observation point. The field of view of the mirror electron microscope had a diameter of 100 μm.

From the image captured at each observation point, presence/absence of a hidden scratch was confirmed. The number of the observation points at which the hidden scratch was detected was found. The number of the observation points at which the hidden scratch was detected were divided the total number of the observation points to find the ratio of hidden scratches. The results are shown in Table 1.

As seen from examples A through E, in the case where the CMP polishing amount t and the post-mechanical polishing roughness Ra of the main surface fulfill the relationship of Pa×70≤t, the ratio of hidden scratches is less than 50%. As the CMP polishing amount t is larger, the ratio of hidden scratches is smaller. Especially as seen from examples A and B, in the case where the etching with $CF_4$ and the etching with $O_2$ are performed and the relationship of Ra×1000≤t is fulfilled, no hidden scratch is observed.

As seen from a comparison between example B and example E, in the case where the CMP step and the oxidation step are performed at the seine time and also the oxidation step is performed at the same time as the etching step (etching with $O_2$), the ratio of hidden scratches is smaller.

By contrast, as seen from comparative examples A and B, in the case where the relationship of Ra×70≤t is not fulfilled, many hidden scratches are present even though the etching with $CF_4$ and the etching with $O_2$ are performed.

As described above, in this embodiment, the hidden scratches are observed by the mirror electron microscope, and the quality of the single-crystal silicon carbide substrate is evaluated based on the ratio of hidden scratches. In this embodiment, a single-crystal silicon carbide substrate having a ratio of hidden scratches of less than 50%, having a decreased number of processing-derived defects and allowing a high quality silicon carbide semiconductor layer to be epitaxially grown thereon is obtained.

The present invention is preferably usable to produce a single-crystal silicon carbide substrate that is usable to produce various types of semiconductor devices.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

This application is based on Japanese Patent Application No. 2015-013216 filed on Jan. 27, 2015, the entire contents of which are hereby incorporated by reference.

TABLE 1

| | Condition | | | | | | Evaluation result Result at 85 points in the plane |
| --- | --- | --- | --- | --- | --- | --- | --- |
| | Pre-processing | | CMP | | | (pitch: 9 mm) | |
| | (mechanical processing) | | polishing amount | RIE | | | Ratio |
| Sample No. | Ra (nm) | Ra × 70 | t (nm) | $O_2$ gas | $CF_4$ gas | Number of areas | of hidden scratches |
| Example A | 0.5 | 35 | 1000 | Yes | Yes | 0 | 0% |
| Example B | 0.5 | 35 | 500 | Yes | Yes | 0 | 0% |
| Example C | 0.5 | 35 | 500 | Yes | Yes | 1 | 1% |
| Example D | 0.5 | 35 | 100 | Yes | Yes | 39 | 46% |
| Example E | 0.5 | 35 | 500 | No | Yes | 42 | 49% |
| Comparative Ex. A | 0.5 | 35 | 10 | Yes | Yes | 85 | 100% |
| Comparative Ex. B | 1 | 70 | 30 | Yes | Yes | 85 | 100% |
| Comparative Ex. C | 0.5 | 35 | 500 | No | No | 56 | 66% |
| Comparative Ex. D | 0.5 | 35 | 500 | No | No | 75 | 88% |
| Comparative Ex. E | 0.5 | 35 | 500 | No | No | 77 | 91% |
| Comparative Ex. F | 0.5 | 35 | 500 | No | No | 53 | 62% |

What is claimed is:

1. A single-crystal silicon carbide substrate, having a main surface having a surface roughness of Ra≤1 nm, and having a ratio of hidden scratches of more than 0% and less than 50%, wherein in the case where the main surface is arbitrary observed at 50 or more observation points with a field of view having a diameter of 100 μm, the ratio of hidden scratches is defined by a value obtained by dividing the number of the observation points at which a striped hidden scratch having a length of at least 50 μm by the total number of the observation points, wherein the single-crystal silicon carbide substrate has an equipotential surface of the main surface, the equipotential surface having convexed or concaved portions at the hidden scratches.

2. The single-crystal silicon carbide substrate according to claim 1, wherein the observation of the main surface is performed based on capture images of the main surface of the single-crystal silicon carbide substrate by a mirror electron microscope.

3. The single-crystal silicon carbide substrate according to claim 2, wherein in the case where the main surface of the single-crystal silicon carbide substrate is irradiated with an electron beam at an accelerated voltage of 5 keV or less in order to capture the image of the main surface by the mirror electron microscope, the main surface is not charged up.

4. The single-crystal silicon carbide substrate according to claim 1, wherein the ratio of hidden scratches is determined based on observation of a main surface of a single-crystal silicon carbide substrate by a mirror electron microscope with an electron beam or an electron beam and an ultraviolet ray.

5. The single-crystal silicon carbide substrate according to claim 4, wherein the ultraviolet ray has an energy larger than, or equal to, a bandgap of a material forming the single-crystal silicon carbide substrate to be inspected.

6. The single-crystal silicon carbide substrate according to claim 4, wherein the main surface of the single-crystal silicon carbide substrate has a surface roughness of 0.2 nm or less.

7. The single-crystal silicon carbide substrate according to claim 4, wherein the main surface of the single-crystal silicon carbide substrate has an oxide layer having a thickness of 5 nm or less.

8. The single-crystal silicon carbide substrate according to claim 1, wherein the hidden scratches comprise charges.

* * * * *